US00PP24476P2

(12) United States Plant Patent
Kristensen

(10) Patent No.: US PP24,476 P2
(45) Date of Patent: May 20, 2014

(54) *OSTEOSPERMUM* PLANT NAMED 'SAKOST8366'

(50) Latin Name: *Osteospermum hybrida*
Varietal Denomination: SAKOST8366

(71) Applicant: Sakata Ornamentals Europe A/S, Marslev (DK)

(72) Inventor: Niels G. Kristensen, Silkeborg (DK)

(73) Assignee: Sakata Ornamentals Europe A/S, Marslev (DK)

( * ) Notice: Subject to any disclaimer, the term of this patent is extended or adjusted under 35 U.S.C. 154(b) by 0 days.

(21) Appl. No.: 13/986,015

(22) Filed: Mar. 22, 2013

(51) Int. Cl.
*A01H 5/00* (2006.01)

(52) U.S. Cl.
USPC ..... Plt./360

(58) Field of Classification Search
USPC ..... Plt./360
See application file for complete search history.

(56) References Cited

U.S. PATENT DOCUMENTS

PP13,321 P2 * 12/2002 Sorensen ..... Plt./360

* cited by examiner

*Primary Examiner* — Anne Grunberg
*Assistant Examiner* — Keith Robinson
(74) *Attorney, Agent, or Firm* — James M. Weatherly; Cochran Freund & Young LLC

(57) ABSTRACT

A new *Osteospermum* plant particularly distinguished by having white and pink flowers with light gray disc florets as well as a fairly compact and very well-branching plant growth habit, is disclosed.

1 Drawing Sheet

Genus and species: *Osteospermum hybrida.*
Variety denomination: 'SAKOST8366'.

BACKGROUND OF THE NEW PLANT

The present invention comprises a new and distinct variety of *Osteospermum*, botanically known as *Osteospermum hybrida*, and hereinafter referred to by the variety name 'SAKOST8366'. 'SAKOST8366' originated from a hybridization of commercial *Osteospermum* line 'SAKOST8202' also known as CAPE DAISY™ 'Soft Pink' (U.S. patent application Ser. No. 13/134,031) and commercial *Osteospermum* line 'SAKOST8201' also known as CAPE DAISY™ 'Purple Illumination' (U.S. patent application Ser. No. 13/068,016) in Marslev, Denmark. The female parent, 'SAKOST8202' has light pink colored flowers (young flowers have a pinkish-white flower color) with light gray disc florets. The male parent, 'SAKOST8201' has white with purple flowers and violet-blue disc florets.

In May 2008 the two *Osteospermum* parental lines 'SAKOST8202' and 'SAKOST8201' were crossed and seeds were obtained. The seeds were sown and plants were grown in pots for evaluation. In February 2009, a plant line was selected which had white and pink flowers with light gray disc florets as well as a fairly compact and very well-branching plant growth habit.

In February 2009, the line was vegetatively propagated by cuttings and re-evaluated in an open field and a greenhouse. The selected line was given the breeder code number '209144' and the stability of the distinct characteristics of this variety were confirmed.

In June 2009, plants of line '209144' were evaluated again in pots and in an open field. The variety was found to reproduce true to type in successive generations of asexual propagation via vegetative cuttings and given the name 'SAKOST8366'.

SUMMARY

The following are the most outstanding and distinguishing characteristics of this new variety when grown under normal horticultural practices in Salinas, Calif.

1. White and pink flowers with light gray disc florets; and
2. Fairly compact and very well-branching plant growth habit.

DESCRIPTION OF THE PHOTOGRAPHS

This new *Osteospermum* plant is illustrated by the accompanying photographs which show the plant's overall plant habit including form, foliage, and flowers. The photographs are of a twelve month old plant from transplant grown in 8-inch pots from rooted cuttings in Salinas, Calif. under greenhouse conditions in the fall of 2012. The colors shown are as true as can be reasonably obtained by conventional photographic procedures.

DESCRIPTION OF THE NEW VARIETY

Figure 1:
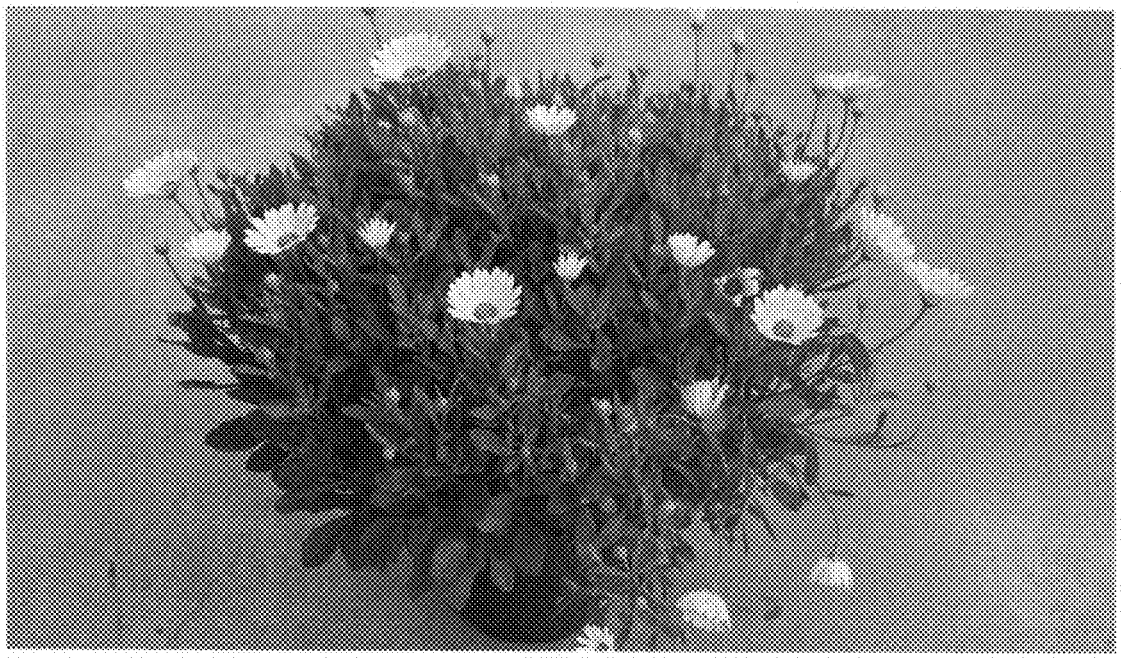
FIG. 1 shows the overall plant habit of the plant grown in a pot.
Figure 2:
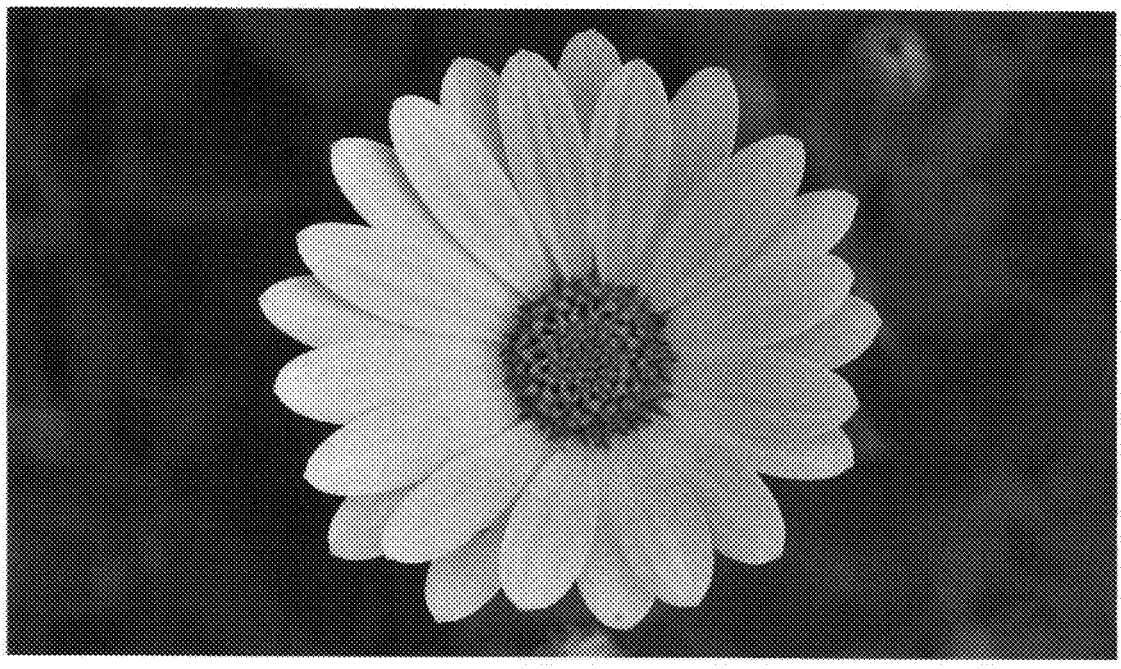
FIG. 2 shows the mature inflorescence of the plant.

The following detailed descriptions set forth the distinctive characteristics of 'SAKOST8366'. The data which define these characteristics were collected from asexual reproductions carried out in Salinas, Calif. Data was collected on twelve-month-old plants from transplant grown in 8-inch pots from rooted cuttings in Salinas, Calif. under greenhouse conditions in the fall of 2012. Color references are to The R.H.S. Colour Chart of The Royal Horticultural Society of London (R.H.S.), 4th edition. Anatomic labels are from The Cambridge Illustrated Glossary of Botanical Terms, by M. Hickey and C. King, Cambridge University Press.

Classification:

*Family.*—Compositae.

*Botanical.*—*Osteospermum hybrida.*

*Common.*—*Osteospermum*, Cape Daisy, South African Daisy.

*Designation.*—'SAKOST8366'.

Parentage:

*Female parent.*—*Osteospermum* line 'SAKOST8202' (U.S. patent application Ser. No. 13/134,031).

*Male parent.*—*Osteospermum* line 'SAKOST8201' (U.S. patent application Ser. No. 13/068,016).

Growth:

*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of Dip 'N Grow root inducing solution in water. The trays are misted hourly during rooting.

*Environmental conditions for plant growth.*—Rooted cuttings are transplanted to pots with a 16 cm diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 cm to 10 cm in height they are pinched back to 5 to 6 leaves to promote branching. Spring and summer daytime high temperatures in Salinas, Calif. where the data was collected, range from 16° C. to 25° C.

*Time to bloom from propagation.*—Approximately four weeks when rooted vegetative cuttings are transferred to a 5-inch diameter pot. Flowering season is in the spring, summer and fall in the United States. Vernalization is not required to induce flowering.

Plant description:

*Habit.*—Fairly compact and very well-branching.

*Life cycle.*—Perennial.

*Form.*—Semi-erect.

*Height (from soil line to first node).*—2.0 cm.

*Height (from soil line to top of foliage).*—40.0 cm.

*Width.*—55.0 cm.

Stems:

*General.*—Multiple; circular in cross-section, smooth.

*Stem length (total).*—18.0 cm.

*Diameter.*—0.4 cm.

*Internode length.*—1.5 cm.

*Color.*—RHS 144B (Yellow-Green) with slight anthocyanin.

*Anthocyanin color.*—RHS 187A (Greyed-Purple).

*Pubescence.*—Light. Color: RHS N155A (White). Shape: Short, hair-like fibers.

Branches:

*General.*—Circular in cross-section, smooth.

*Number of main branches.*—One.

*Total number of branches.*—Twelve.

*Length.*—28.0 cm, approximately 2.0 cm from soil line to first node, 3.0 cm between first and second nodes.

*Diameter.*—1.0 cm.

*Internode length.*—2.0 cm.

*Color.*—Closest to RHS 144B (Yellow-Green) with slight anthocyanin.

*Pubescence.*—Absent.

Leaves:

*Arrangement.*—Alternate.

*Shape.*—Oblanceolate.

*Apex.*—Acute.

*Base.*—Attenuate.

*Margin.*—Serrate.

*Venation.*—Pinnate.

*Surface (both surfaces).*—Dull.

*Surface pubescence (both surfaces).*—Slight.

*Surface pubescence color (both surfaces).*—RHS N155A (White).

*Attachment.*—Decurrant.

*Length.*—7.0 cm.

*Width.*—2.5 cm.

*Thickness.*—Less than 0.1 cm.

*Color.*—Upper surface: RHS 147A (Yellow-Green). Lower surface: RHS 147B (Yellow-Green).

*Venation color.*—Upper surface: RHS 147C (Yellow-Green). Lower surface: RHS 147C (Yellow-Green).

Inflorescence:

*Number per plant.*—40 to 50 in bloom.

*Type.*—Capitulum (head); disc florets are perfect and ray florets are carpellate.

*Flowering habit.*—Determinate.

*Lastingness of inflorescence on plant.*—3 to 4 days.

*Fragrance.*—Absent.

*Seed production.*—None observed.

*Diameter.*—5.0 cm.

*Depth.*—2.0 cm.

*Petal (ray floret) number.*—19 per inflorescence.

*Disc diameter.*—1.5 cm.

*Disc floret number.*—100 to 120 per inflorescence.

*Peduncle length.*—5.5 cm from inflorescence to first node.

*Peduncle diameter.*—0.2 cm.

*Peduncle color.*—RHS 144A (Yellow-Green) with slight anthocyanin.

*Anthocyanin color.*—RHS 187A (Greyed-Purple).

*Peduncle texture.*—Dull; slight pubescence.

*Phyllaries.*—Arrangement: 24 per inflorescence; free; arranged symmetrically. Length: 1.0 cm. Width: 0.2 cm. Apex: Acute. Margin: Entire. Shape: Linear; acute. Color: Upper surface: RHS 143A (Green). Lower surface: RHS 143B (Green).

Ray florets (ligules):

*Corolla.*—One petal per ray floret; only the outer row of florets are the ray florets.

*Number of ray florets.*—21 per inflorescence.

*Length.*—3.0 cm.

*Width.*—0.8 cm.

*Shape.*—Lanceolate.

*Apex.*—Acute.

*Margin.*—Entire.

*Color.*—Upper surface: Closest to RHS 65B (Red-Purple). Lower surface: RHS 6D (Yellow).

*Pubescence.*—Glabrous.

Disc florets:

*Color.*—RHS 188A (Greyed-Green).

*Shape.*—Tubular.

*Apex.*—Pointed.

*Texture.*—Dull, pubescent.

*Size.*—Length: 0.9 cm. Width: 0.1 cm.

Reproductive organs:

*Ovary.*—Superior.

*Pistil form.*—One style with two stigma branches.

*Pistil length.*—0.6 cm.

*Stigma color.*—RHS N186A (Greyed-Purple).

*Style color.*—RHS 6D (Yellow). Stamens: 5; fused into a single tube. Anther color: RHS 187A (Greyed-Purple). Pollen color: RHS 17A (Yellow-Orange). Filament color: RHS 155A (White).

Disease and insect resistance: No known resistance or susceptibility.

COMPARISON WITH PARENTAL LINES AND KNOWN VARIETY

'SAKOST8366' is a distinct variety of *Osteospermum* is a distinct variety of *Osteospermum* having white and pink flowers with light gray disc florets as well as a fairly compact and very well-branching plant growth habit; 'SAKOST8366' is distinguished from its parents as described in Table 1 (color references are to The Royal Horticultural Society Colour Chart, 4$^{th}$ edition):

TABLE 1

Comparison with Parental Lines

| Characteristic | 'SAKOST8366' | Female Parent 'SAKOST8202' | Male Parent 'SAKOST8201' |
|---|---|---|---|
| Ray floret (ligule) color, upper surface: | Closest to RHS 65B (Red-Purple) | RHS 62C (Red-Purple) with young flowers of RHS 155B (White) | RHS 155D (White) with RHS 72B (Red-Purple) stripes and at base |

TABLE 1-continued

Comparison with Parental Lines

| Characteristic | 'SAKOST8366' | Female Parent 'SAKOST8202' | Male Parent 'SAKOST8201' |
|---|---|---|---|
| Disc floret color: | RHS 188A (Greyed-Green) | RHS N187A (Greyed-Purple) | RHS 94B (Violet-Blue) |

'SAKOST8366' is a distinct variety of *Osteospermum* having white and pink flowers with light gray disc florets as well as a fairly compact and very well-branching plant growth habit. 'SAKOST8366' is most similar to the *Osteospermum* plant named 'SAKOST8202' (U.S. patent application Ser. No. 13/134,031). Differences between the two varieties are described in Table 2 (color references are to The Royal Horticultural Society Colour Chart, 4$^{th}$ edition):

TABLE 2

Comparison with Similar Variety

| Characteristic | 'SAKOST8366' | 'SAKOST8202' |
|---|---|---|
| Ray floret (ligule) color, upper surface: | Closest to RHS 65B (Red-Purple) | RHS 62C (Red-Purple) with young flowers of RHS 155B (White) |
| Ray floret (ligule) color, lower surface: | Closest to RHS 6D (Yellow) | RHS 151B (Yellow-Green) |
| Disc floret color: | RHS 188A (Greyed-Green) | RHS N187A (Greyed-Purple) |
| Plant growth habit: | Fairly compact | Semi-erect |

I claim:

1. A new and distinct variety of *Osteospermum* plant as shown and described herein.

* * * * *